United States Patent [19]

Adams et al.

[11] 4,053,639

[45] Oct. 11, 1977

[54] THERAPEUTICALLY ACTIVE PHENYLALKANE DERIVATIVES

[75] Inventors: Stewart Sanders Adams; Bernard John Armitage; John Stuart Nicholson, all of Nottingham, England; Antonio Ribera Blancafort, Madrid, Spain

[73] Assignee: The Boots Company Limited, Nottingham, England

[21] Appl. No.: 391,759

[22] Filed: Oct. 4, 1973

Related U.S. Application Data

[60] Continuation-in-part of Ser. No. 308,558, Nov. 12, 1972, Pat. No. 3,793,457, which is a division of Ser. No. 845,033, July 25, 1969, Pat. No. 3,755,427, which is a continuation-in-part of Ser. No. 425,624, Jan. 14, 1965, abandoned.

[51] Int. Cl.$^2$ .................... C07C 31/34; A01N 9/24; A61K 31/045
[52] U.S. Cl. ................... 424/343; 260/618 D
[58] Field of Search .............. 260/618 R, 618 D; 424/343

[56] References Cited

U.S. PATENT DOCUMENTS

| 2,634,302 | 4/1953 | Seymour et al. | 260/618 R |
|---|---|---|---|
| 3,385,886 | 5/1968 | Nicholson et al. | 260/618 D |
| 3,624,142 | 11/1971 | Shen et al. | 260/618 R |
| 3,793,457 | 2/1974 | Adams et al. | 424/317 |
| 3,801,654 | 4/1974 | Seeger et al. | 424/343 |
| 3,859,256 | 1/1975 | Teufel et al. | 424/343 |
| 3,859,363 | 1/1975 | Teufel et al. | 260/618 R |

*Primary Examiner*—James O. Thomas, Jr.
*Assistant Examiner*—James H. Reamer
*Attorney, Agent, or Firm*—Gordon W. Hueschen

[57] ABSTRACT

2-(2-Fluoro-4-biphenylyl)propan-1-ol, 2-(2'-Fluoro-4-biphenylyl)propan-1-ol and 2-(2,2'-Difluoro-4-biphenylyl)propan-1-ol possessing great anti-inflammatory, analgesic and antipyretic activities.

8 Claims, No Drawings

THERAPEUTICALLY ACTIVE PHENYLALKANE DERIVATIVES

This application is a continuation-in-part of Ser. No. 308,558, filed Nov. 21, 1972, now U.S. Pat. No. 3,793,457, issued Feb. 19, 1974, which in turn is a division of Ser. No. 845,033 filed July 25, 1969, now U.S. Pat. No. 3,755,427, issued Aug. 28, 1973 which in turn is a continuation-in-part of Ser. No. 425,624, filed January 14, 1965, now abandoned.

In Ser. No. 845,033, now U.S. Pat. No. 3,755,427, the following compounds are claimed:

2-(2-fluoro-4-biphenylyl) propionic acid
2-(2'-fluoro-4-biphenylyl) propionic acid and
2(2,2'-difluoro-4-biphenylyl) propionic acid These compounds have very good anti-inflammatory properties. It is generally assumed with anti-inflammatory compounds of the biphenylylalkane series that acids have much greater activity than the various other types of compounds.

We have surprisingly found that the related alcohols of the above three acids have only a slightly lower anti-inflammatory activity than the acids.

The invention provides novel compounds selected from the group consisting of 2-(2-fluoro-4-biphenylyl) propan-1-ol
2-(2'-fluoro-4-biphenylyl) propan-1-ol and
2-(2,2'-difluoro-4-biphenylyl) propan-1-ol These compounds possess anti-inflammatory properties and also possess analgesic and antipyretic properties and are useful for the treatment of inflammatory conditions and also conditions of pain and pyretic conditions, individually or in any combination.

It is believed that these compounds are metabolised by the animal body and converted by the body into the corresponding acid.

These compounds may conveniently be prepared by reducing the appropriate substituted 4-biphenylylpropionic acid or an ester thereof. The acid itself may conveniently be prepared by reacting an ester of the appropriate substituted 4-biphenylylacetic acid with diethyl carbonate to give a malonic acid ester, methylating the sodium derivative of this ester, hydrolysing the ester and decarboxylating the resulting acid. For example,

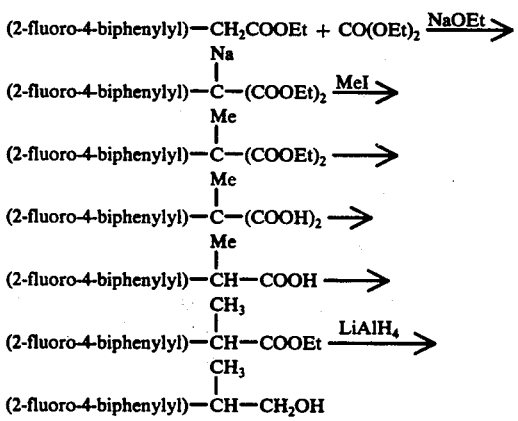

The anti-inflammatory activity of the compounds of the invention has been determined in experimental animals using a pharmacological test which is known to be capable of characterising compounds possessing aspirin-like anti-inflammatory activity.

The test used was the method of Adams and Cobb, Nature, 1958, 181, 773. Female guinea pigs (Tuck strain) weighing 500–900 g. were fasted overnight and an area of the back depilated on the morning of the test. The animals were dosed with the compounds under test and 30 minutes later a part of the depilated area was exposed for 20 seconds to ultraviolet radiation from a Hanovia "Kromayer" lamp applied directly to the skin. Two hours later, the degree of erythema (redness) was visually determined and given a score of 0, 1, 2, 3, or 4 by a trained observer who was unaware of the dosage schedules. The compounds were administered orally in 10% acacia mucilage, control animals (giving a score of 4) receiving the mucilage only.

In the case of aspirin, three dosage rates of 160, 80 and 40 mg./kg. were used and in the cases of the compounds of the invention seven dosage rates of 2.0, 1.0, 0.5, 0.25, 0.125, 0.062 and 0.031 mg./kg. were used. Ten guinea pigs were employed for each dosage level and as controls.

Dose response curves for each compound were plotted (i.e. dosage against degree of erythema) and approximate $E.D._{50}$'s in mg./kg. were determined from these curves; the $E.D._{50}$ is that dose of a compound which reduces the degree of erythema scored as 4 (as given by the controls) by a half i.e. to a degree of erythema scored as 2. The activity of the compounds of the invention was then determined in terms of the potency of aspirin.

The results are shown in the following table.

TABLE

| Compound | Anti-inflammatory activity in terms of the potency of aspirin. |
| --- | --- |
| Aspirin | 1 |
| 2-(2-Fluoro-4-biphenylyl)propan-1-ol | 160 |
| 2-(2'-Fluoro-4-biphenylyl)propan-1-ol | 160 |
| 2-(2,2'-Difluoro-4-biphenylyl)propan-1-ol | 160 |

As well as anti-inflammatory activity, the analgesic activity is determined by a modification of the method of Randall and Selitto, Arch. int. Pharmacodyn. 1957, 111, 409, in which the analgesic effect of the drugs is compared with aspirin by determing the increase in pain threshold when pressure is applied to the foot. In the modification pressure is applied to the plantar surface of the foot by means of a vertically-fixed glass syringe bearing a conical perspex attachment on the plunger instead of a bullet-shaped wooden plug.

The antipyretic activity is determined in rats in which the body temperature is raised by a subcutaneous injection of a yeast suspension. Comparison of the compounds under test is made with graded doses of aspirin.

The compounds of the invention may be administered in the conventional manner of aspirin or usual manner for other anti-inflammatory, analgesic and antipyretic agents, for example orally, topically, rectally or parenterally, preferably orally, the optimum dosage rate varying with the choice of active ingredient and the route of administration. The unit dose may vary from 1 mg. to 500 mg. per subject per day; for oral administration the dosage rate is preferably 5–250 mg. per subject per day, most preferably 10–60 mg. per subject per day, optionally in divided doses.

In use, the compounds of the invention are administered in conventional formulations and accordingly the invention also provides therapeutic compositions which comprise a compound of the invention in association with pharmaceutical excipients known for the production of compositions for oral, topical, rectal or parenteral administration. These compositions preferably contain 0.1–90% by weight of a compound of the invention.

Compositions for oral administration are the preferred compositions of the invention, and these are the conventional pharmaceutical forms for such administration, such as for example tablets, capsules, lozenges, powders, effervescent granules, syrups and aqueous and oily suspensions. The excipients used in the preparation of these compositions are the excipients known in the pharmacist's art. Thus in the preparation of tablets, typical excipients include disintegrating agents, e.g., maize starch and lubricating agents, e.g., magnesium stearate; in the preparation of capsules, standard gelatin capsules may be used containing the active ingredient alone or admixed with a diluent. The liquid compositions may comprise as excipients water and sucrose to provide syrups, water, dispersing agents and suspending agents, e.g., sodium carboxymethylcellulose to provide aqueous suspensions and a non-toxic oil, e.g. a vegetable oil such as arachis oil and a suspending agent to provide oily suspensions.

Compositions for rectal administration are the conventional pharmaceutical forms for such administration, such as for example suppositories with cocoa butter or polyethylene glycol bases.

Compositions for topical use are the conventional pharmaceutical forms for such application, such as ointments, creams and lotions. Ointments and creams may be water miscible or water-immiscible in character and include emulsions prepared from emulsifying waxes and oils and those prepared from water miscible polyethylene glycols. Lotions may comprise a solution in an aliphatic alcohol with 1–4 carbon atoms which may contain a small proportion of water.

Compositions for parenteral administration are the conventional pharmaceutical forms for such administration, for example sterile suspensions in aqueous or oily media or sterile solutions in propylene glycol.

In some formulations it may be beneficial to use compounds of the invention in the form of particles of very simall size, such as for example, as obtained by fluid energy milling, e.g., micronizing.

The invention further provides a method of treating inflammatory conditions, conditions of pain and pyretic conditions, individually or in any combination, which comprises administering a compound of the invention, preferably orally.

The products of the present invention may of course be employed in combination with each other, or with other active anti-inflammatory agents, analgesics and anti-pyretic agents, or with other drugs, as is already conventional in the art for other existing anti-inflammatory, analgesic and antipyretic materials such as aspirin.

The following non-limitative example illustrate the invention.

EXAMPLE 1

2-(2-Fluoro-4-biphenylyl)propan-1-ol

A mixture of 4-acetyl-2-fluorobiphenyl, m.p. 95°–96° C., (73.5 g.) [prepared from 4-bromo-3-nitroacetophenone (Oelschlager, Ann., 1961, 641, 81) via 4-acetyl-2-nitrobiphenyl, m.p. 106°–108° C.

(Ullman reaction), 4-acetyl-2-aminobiphenyl, m.p. 124°–125° C. (reduction), and finally the Schiemann reaction], sulphur (17.4 g.) and morpholine (87 ml.) was refluxed for 16.5 hours, and then the resulting thiomorpholide was hydrolysed by refluxing with glacial acetic acid (340 ml.), concentrated sulphuric acid (54 ml.) and water (78 ml.) for 24 hours. The cooled solution was diluted with water, and the precipitated crude 2-fluoro-4-biphenylylacetic acid was collected. (A sample was purified by recrystallisation to give m.p. 143°–144.5° C.; Found: C, 73.2; H, 4.8. $C_{14}H_{11}FO_2$ requires C, 73.1; H, 4.8%).

A sodium carbonate solution of the crude acetic acid was washed with ether and then acidified with hydrochloric acid; the required acid was isolated via an ether extraction and was esterified by refluxing for 6 hours with ethanol (370 ml.) and concentrated sulphuric acid (15 ml.). Excess alcohol was distilled, the residue diluted with water and the required ester isolated in ether.

Distillation finally gave ethyl 2-fluoro-4-biphenylylacetate, b.p. 134°–136° C./0.25 mm.

This ester (70 g.) and diethyl carbonate (250 ml.) were stirred at 90°–100° C. whilst a solution of sodium ethoxide [from sodium (7.8 g.) and ethanol (154 ml.)] was added over 1 hour. During addition, ethanol was allowed to distil and after addition distillation was continued until the column head temperature reached 124° C. After cooling the solution to 90° C., dimethyl sulphate (33 ml.) was added followed by a further 85 ml. of diethyl carbonate. This solution was stirred and refluxed for 1 hour and then, when ice cool, was diluted with water and acetic acid (10 ml.). The malonate was isolated in ether and fractionally distilled to yield a fraction boiling at 148°–153° C./0.75 mm., identified as the alphamethyl malonate. This was hydrolysed by refluxing for 1 hour with 2.5N sodium hydroxide (350 ml.) and alcohol (175 ml.), excess alcohol was distilled and the residual suspension of sodium salt was acidified with hydrochloric acid to give a precipitate of the alpha-methyl malonic acid. This was decarboxylated by heating to 180°–200° C. for 30 minutes and recrystallised from petroleum ether (b.p. 80°–100° C.) to give 2-(2-fluoro-4-biphenylyl)propionic acid, m.p. 110°–111° C. (Found: C, 74.2; H, 5.4. $C_{15}H_{13}FO_2$ requires C, 73.8; H, 5.3%).

A mixture of this acid (4 g.), concentrated sulphuric acid (1.0 ml.) and absolute ethanol (30 ml.) was refluxed for 21 hours. The solvent was evaporated, the residue diluted with water and extracted with ether. The extracts were washed with aqueous sodium carbonate, water, dried and distilled to give ethyl 2-(2-fluoro-4-biphenylyl) propionate, b.p. 142°–4° C./0.4 mm. (Found: C, 74.85; H, 6.4. $C_{17}H_{17}FO_2$ requires: C,75.0; H, 6.4%).

A solution of this ester (2.62 g.) in dry ether was added over 5 minutes to a stirred suspension of lithium aluminium hydride (0.25 g.) in dry ether (15 ml.). The mixture was refluxed for 1 hour before decomposing with wet ether and then water. The mixture was poured onto a mixture of ice and dilute sulphuric acid and then extracted with ether. The extracts were distilled to give 2-(2-fluoro-4-biphenylyl)propan-1-ol, b.p. 124°–6° C./0.05 mm, which solidified on standing, m.p. 61°–63° C. (Found: C, 78.3; H,6.5. $C_{15}H_{15}FO$ requires C,78.3; H,6.5%).

EXAMPLE 2

2-(2'-Fluoro-4-biphenylyl)propan-1-ol

4-Acetyl-2'-fluorobiphenyl, b.p. 145°-150° C./2 mm. (179.5 g.) (Renoll, *J. Amer. Chem. Soc.*, 1946, 68, 1159), morpholine (133 ml.) and sulphur (42.4 g.) were refluxed for 16 hours, cooled, and a mixture of glacial acetic acid (532 ml.), concentrated sulphuric acid (83 ml.) and water (126 ml.) added. This mixture was refluxed for 24 hours, cooled, diluted with water and the precipitated crude 2'-fluoro-4-biphenylylacetic acid was collected. (A sample recrystallised from petroleum ether b.p. 80° C.–100° C. had a m.p. of 99°–101° C.).

A sodium carbonate solution of the crude acetic acid was filtered and the filtrate acidified with dilute hydrochloric acid; the required acetic acid was isolated via an ether extraction and was esterified by refluxing for 6 hours with ethanol (600 ml.) and concentrated sulphuric acid (27 ml.). Excess alcohol was distilled in vacuo and the required ester isolated in ether. Distillation finally gave ethyl 2'-fluoro-4-biphenylylacetate, b.p. 144° C./0.25 mm., m.p. 42°-48° C. (Found: C, 74.6; H, 6.1. $C_{16}H_{15}FO_2$ requires C, 74.4; H, 5.8%).

Sodium ethoxide [from sodium (15.6 g.) and ethanol (308 ml.)] was added over 65 minutes to a stirred mixture of ethyl 2'-fluoro-4-biphenylylacetate (140 g.) and diethyl carbonate (500 ml.) maintained at 90°-100° C. During the addition, ethanol was allowed to distil and after addition distillation was continued until the column head temperature reached 124° C. After 15 minutes at this temperature diethyl carbonate (150 ml.) was added and the slurry cooled to 90° C. Dimethyl sulphate (66 ml.) and diethyl carbonate (20 ml.) were then added dropwise, the mixture was stirred and refluxed for 1 hour, cooled to room temperature and diluted with water (500 ml.) containing glacial acetic acid (10 ml.). The malonate was isolated in ether and distilled, b.p. 168°-170° C./0.3 mm; the distillate was melted and diluted with petroleum ether, b.p. 40°-60° C. (300 ml.), cooled to 20° C. and the resulting solid ethyl 2-(2'-fluoro-4-biphenylyl)-2-methylmalonate collected, m.p. 58°-60.5° C. (Found: C, 69.4; H, 6.1. $C_{20}H_{21}FO_4$ requires C, 69.7; H, 6.1%).

This ester (139 g.) was hydrolysed by refluxing for 1 hour with sodium hydroxide (660 ml. of 2.5N) and alcohol (330 ml.). The resulting solution was concentrated in vacuo until a distillate of about 300 ml. had been collected, and the warm residual solution was acidified with concentrated hydrochloric acid to give a precipitate of the alpha-methylmalonic acid. This was decarboxylated by heating at 190°-200° C. for 25 minutes and recrystallised from benzene (45 ml.)/petroleum ether, b.p. 80°-100° C. (135 ml.) to give 2-(2'-fluoro-4-biphenylyl)propionic acid, m.p. 94.5°-97° C. (Found: C, 73.7; H, 5.5 $C_{15}H_{13}FO_2$ requires C, 73.8; H, 5.3%).

A solution of this acid (18.3 g.) in dry ether (60 ml.) was added dropwise to a mixture of lithium aluminium hydride (2.25 g.) and dry ether (30 ml.) stirred under a nitrogen atomosphere. During the addition the solvent refluxed and when the addition was complete the mixture was stirred at room temperature for 45 minutes. It was then cooled in ice and a 10% aqueous solution of ammonium chloride (100 ml.) was added. Ether was added to dissolve the product and the mixture was filtered. The filtrate was extracted with ether and the extracts were combined, washed with water, aqueous potassium carbonate, water and dried over magnesium sulphate. The ether was evaporated leaving a turbid oil which rapidly solidified. This was recrystallised from light petroleum (b.p. 60°-80° C.) to give 2-(2'-fluoro-4-biphenylyl)propan-1-ol, m.p. 73°-74° C. (Found: C, 78.4 H, 6.3 $C_{15}H_{15}FO$ requires C, 78.3; H, 6.5%).

EXAMPLE 3

2-(2'-Difluoro-4-biphenylyl)propan-1-ol

2-Bromonitrobenzene (*Beilstein*, Vol. 5, p.247; 58g) and 2,5-dibromonitrobenzene (*Beilstein*, vol. 5 p.250; 81g) in nitrobenzene (250 ml.) were heated at 170°-180° C. while copper powder (70 g.) was added over 15 minutes. The reaction mixture was stirred at 180° C. for 15 minutes, cooled and filtered, and the filtrate evaporated under reduced pressure. The residue was extracted into chloroform, the extract dried and evaporated, and the solid recrystallised several times from methanol to give 4-bromo-2,2'-dinitrobiphenyl, m.p. 145°-147° C. (Found: Br, 24.6 $C_{12}H_7BrN_2O_4$ requires Br, 24.8%).

4-Bromo-2,2'-dinitrobiphenyl (50 g.) was Soxhlet extracted into a stirred refluxing mixture of alcohol (750 ml.), stannous chloride (330 g.) and concentrated hydrochloric acid (350 ml.). After refluxing for 30 minutes, the solvent was removed by distillation and the residue poured on to ice (1 kg.) and 5 N sodium hydroxide (500 ml.). More alkali was added until the inorganic solids dissolved. The product was isolated in ether; distillation (b.p. 140°-190° C./0.2 mm.) followed by crystallisation from petroleum ether, b.p. 62°-68° C., gave 4-bromo-2,2'-diaminobiphenyl, m.p. 61°-62° C. (Found: Br, 30.7; N, 10.7. $C_{12}H_{11}BrN_2$ requires Br, 30.4; N, 10.6%). This compound (10 g.) was dissolved in a mixture of tetrahydrofuran (20 ml.) and fluoroboric acid (38 ml. of 40%) and treated with a solution of sodium nitrite (6 g.) in water (10 ml.) at 0° C. After stirring at 0° C. for 15 minutes, the solid was filtered off, washed with 4% fluoroboric acid, ether/ethanol (9:1) and dry ether, and dried over phosphorus pentoxide. This solid fluoroborate was suspended in dry xylene (100 ml.) and heated under reflux until vigorous evolution of boron trifluoride occurred. Heating was continued for 1 hour after the reaction had subsided, the mixture was cooled and then stirred with 5N sodium hydroxide (100 ml.). The organic layer was evaporated at atmospheric pressure and the residue distilled in vacuo, b.p. 135°-140° C./3 mm. Recrystallisation from petroleum ether, b.p. 40°-60° C., at −20° C. gave 4-bromo-2,2'-difluorobiphenyl, m.p. 45°-46° C. (Found: C, 53.6; H, 2.7; Br, 29.3 $C_{12}H_7BrF_2$ requires C, 53.5; H, 2.6; Br, 29.8%).

This compound (4 g.), cuprous cyanide (3.28 g.) and dimethylformamide (25 ml.) were stirred under reflux for 4 hours. The solution was then poured into a mixture of ferric chloride (6 g.), water (20 ml.) and concentrated hydrochloric acid (2.5 ml.). The mixture was kept at 70°-80° C. for 20 minutes, cooled in ice and the solid collected. Recrystallisation from petroleum ether, b.p. 80°-100° C., gave 4-cyano-2,2'-difluorobiphenyl, m.p. 78°-79° C. (Found: C, 72.8; H, 3.6. $C_{13}H_7F_2N$ requires C, 72.6; H, 3.3%).

This compound (4.76 g.) in ether (100 ml.) was added to methyl magnesium iodide made from magnesium (2.64 g.), methyl iodide (6.2 ml.) and ether (50 ml.). After overnight refluxing, 2N hydrochloric acid (100 ml.) was added at a rate such as to keep the ether distilling off gently. After cooling, the mixture was extracted with methylene chloride; washing with sodium bicarbonate solution, evaporation and crystallisation at −25° C. from petroleum ether, b.p. 40°–60° C., gave crude 4-acetyl-2,2'-difluorobiphenyl.

This compound (2.4 g.), sulphur (0.65 g.) and morpholine (7.5 ml.) were refluxed overnight; the solution was cooled and glacial acetic acid (25 ml.), water 7.5 ml.) and concentrated sulphuric acid (5 ml.) added. After refluxing for 7 hours, the mixture was poured into water (250 ml.) and the product isolated in ether. Evaporation and crystallisation from petroleum ether, b.p. 62°–68° C., gave 2,2'-difluoro-4-biphenylylacetic acid, m.p. 126°–127° C. (Found: C, 67.7; H, 4.5. $C_{14}H_{10}F_2O_2$ requires C, 67.7; H, 4.0%).

This acid (8.1 g.) was esterified in the conventional manner using ethanol/concentrated sulphuric acid to give ethyl 2,2'-difluoro-4-biphenylylacetate, b.p. 120°–124° C./0.05 mm. This ester (7.47 g.) and diethyl carbonate (75 ml.) were stirred at 90°–100° C. whilst a solution of sodium ethoxide [from sodium (0.78 g.) and ethanol (50 ml.)] was added over 10 minutes. During addition, ethanol was allowed to distil and after addition, distillation was continued until the column head temperature reached 124° C. After cooling to 90° C., dimethyl sulphate (4.3 g.) was added and the mixture refluxed for 1 hour, cooled, diluted with water and neutralised with acetic acid. The malonate was isolated in ether and distilled to give diethyl 2-(2,2'-difluoro-4-biphenylyl)-2-methylmalonate, b.p. 160°–164° C./0.1 mm.

This compound (3.19 g.) was refluxed for 1 hour with ethanol (10 ml.) and 2.5 N sodium hydroxide (25 ml.), excess alcohol was distilled and the residue acidified with hydrochloric acid. The malonic acid thus obtained was decarboxylated by heating at 180° C. for 20 minutes and recrystallised from benzene and from petroleum ether, b.p. 80°–100° C., to give 2-(2,2'-difluoro-4-biphenylyl) propionic acid, m.p. 120.5°–123° C. (Found: C, 68.8; H, 4.7. $C_{15}H_{12}F_2O_2$ requires C, 68.7; H, 4.6%).

A solution of this acid (2.0 g.) in dry ether (25 ml.) was added dropwise to a stirred suspension of lithium aluminium hydride (0.5 g.) in dry ether (20 ml.). The mixture was then refluxed for 1 hour, cooled in ice and decomposed with dilute sulphuric acid. The product was isolated in ether, washed with aqueous potassium carbonate, water, dried over sodium sulphate and evaporated to dryness. The residue was recrystallised from light petroleum (b.p. 60°–80° C.).from sheet) to give 2-(2,2'-difluoro-4-biphenylyl)propan-1-ol, m.p. 80°–82.5° C. (Found: C, 72.7; H, 5.7 $C_{15}H_{14}F_2O$ requires C, 72.5; H, 5.6%).

EXAMPLE 4

Compositions — Hard Gelatin Capsules

No. 5 hard gelatin capsules were prepared each containing the following:

| (a) | 2-(2-fluoro-4-biphenylyl)propan-1-ol | 5 mg. |
|---|---|---|
|  | lactose | 95 mg. |
| (b) | 2-(2-fluoro-4-biphenylyl)propan-1-ol | 5 mg. |
|  | calcium phosphate | 5 mg. |
|  | maize starch | 90 mg. |
| (c) | 2-(2-fluoro-4-biphenylyl)propan-1-ol | 5 mg. |
|  | maize starch ⎫ |  |
|  | lactose ⎬ equal parts |  |
|  | calcium phosphate ⎭ by weight | 95 mg. |

In the same manner, the other compounds of the present invention, namely 2-(2'-fluoro-4-biphenylyl)-propan-1-ol and 2-(2,2'-difluoro-4-biphenylyl)propan-1-ol, are incorporated into composition forms and the composition enclosed in hard gelatin capsules.

When used as described hereinbefore, these compositions of the products of the present invention produce the desired results already fully documented herein.

EXAMPLE 5

Compositions — Tablets

The following mixture (parts by weight) was formed into tablets in conventional manner, each tablet containing 5 mg. of active ingredient:

| 2-(2-fluoro-4-biphenylyl)propan-1-ol | 5 |
|---|---|
| maize starch | 30 |
| lactose | 163 |
| stearic acid | 1 |
| magnesium stearate | 1 |

In the same manner, the other compounds of the invention, namely 2-(2'-fluoro-4-biphenylyl)propan-1-ol and 2(2,2'-difluoro-4-biphenylyl)propan-1-ol, are combined with conventional tableting excipients and binders, and formed into tablets in the conventional manner in a tablet-making device.

When used as described hereinbefore, these compositions of the products of the present invention produce the desired results already fully documented herein.

In the same manner, the compounds of the present invention are incorporated into other conventional compositions and formulations, taking various conventional forms, and administered as previously described to give the desirable relief described, depending upon the physiological abnormality or condition being treated.

We claim:
1. A compound selected from the group consisting of 2-(2-fluoro-4-biphenylyl)propan-1-ol,
2-(2'-fluoro-4-biphenylyl)propan-1-ol and
2-(2,2'-difluoro-4-biphenylyl)propan-1-ol
2. 2-(2-Fluoro-4-biphenylyl)propan-1-ol
3. 2-(2'-Fluoro-4-biphenylyl)propan-1-ol
4. 2-(2,2'-Difluoro-4-biphenylyl)propan-1-ol
5. A therapeutic composition useful in the treatment of pain, inflammation and pyretic conditions which comprises a compound selected from the group consisting of 2-(2-fluoro-4-biphenylyl)propan-1-ol, 2-(2'-fluoro-4-biphenylyl)propan-1-ol and 2-(2,2'-difluoro-4-biphenylyl)propan-1-ol in association with a pharmaceutically acceptable excipient the amount of said compound present in said composition being an effective amount.
6. A method of treating inflammatory conditions which comprises administering to a subject affected with inflammation an effective amount of a compound selected from the group consisting of 2-(2-fluoro-4-biphenylyl)propan-1-ol, 2-(2'-fluoro-4-biphenylyl)propan-1-ol and 2-(2,2'-difluoro-4-biphenylyl)propan-1-ol.
7. A method of treating conditions of pain which comprises administering to a subject suffering from pain an effective amount of a compound selected from the group consisting of 2-(2-fluoro-4-biphenylyl)propan-1-ol, 2-(2'-fluoro-4-biphenylyl)propan-1-ol and 2-(2,2'-difluoro-4-biphenylyl)propan-1-ol.
8. A method of treating pyretic conditions which comprises administering to a subject suffering from pyrexia an effective amount of a compound selected from the group consisting of
2-(2-fluoro-4-biphenylyl)propan-1-ol,
2-(2'-fluoro-4-biphenylyl)propan-1-ol and
2-(2,2'-difluoro-4-biphenylyl)propan-1-ol.

* * * * *